United States Patent
Merli et al.

(10) Patent No.: US 6,852,861 B2
(45) Date of Patent: Feb. 8, 2005

(54) PREPARATION OF 1H-IMIDAZO [4,5-C] QUINOLIN-4-AMINES VIA 1H-IMIDAZO [4,5-C] QUINOLIN-4-PHTHALIMIDE INTERMEDIATES

(75) Inventors: Valeriano Merli, Cremella Lecco (IT); Silvia Mantovani, Lendinara (IT); Stefano Bianchi, Breccia Como (IT)

(73) Assignee: Biogal Gyogyszergyar Rt., Debrecen (HU)

( * ) Notice: Subject to any disclaimer, the term of this patent is extended or adjusted under 35 U.S.C. 154(b) by 0 days.

(21) Appl. No.: 10/626,036

(22) Filed: Jul. 23, 2003

(65) Prior Publication Data

US 2004/0138459 A1 Jul. 15, 2004

Related U.S. Application Data

(60) Provisional application No. 60/397,607, filed on Jul. 23, 2002.

(51) Int. Cl.[7] .............................................. C07D 515/12
(52) U.S. Cl. ......................................................... 546/82
(58) Field of Search ........................................... 546/82

(56) References Cited

U.S. PATENT DOCUMENTS

| | | | |
|---|---|---|---|
| 4,689,338 A | 8/1987 | Gerster | 514/293 |
| 4,689,388 A | 8/1987 | Hirai et al. | 528/104 |
| 4,698,348 A | 10/1987 | Gerster | 514/293 |
| 4,988,815 A | 1/1991 | André et al. | 546/159 |
| 5,238,944 A | 8/1993 | Wick et al. | 514/293 |
| 5,395,937 A | 3/1995 | Nikolaides et al. | 546/82 |
| 5,578,727 A | 11/1996 | Andre et al. | 566/82 |
| 5,602,256 A | 2/1997 | André et al. | 546/180 |
| 5,756,747 A | 5/1998 | Gerster | 546/82 |

FOREIGN PATENT DOCUMENTS

| | | |
|---|---|---|
| EP | 0 145 340 A2 B1 | 6/1985 |
| EP | 0 310 950 A1 B1 | 4/1989 |
| EP | 0 385 630 A2 A3 B1 | 9/1990 |
| JP | 4-193866 | 7/1992 |
| WO | WO 92/06093 | 4/1992 |
| WO | WO 92/15581 | 9/1992 |
| WO | WO 97/48704 | 12/1997 |

*Primary Examiner*—Amelia A. Owens
(74) *Attorney, Agent, or Firm*—Kenyon & Kenyon

(57) ABSTRACT

The invention provides 1H-imidazo(4,5-C)quinolin-4-phthalimide intermediates useful in the synthesis of 1H-imidazo(4,5-C)quinoline-4-amines, particularly Imiquimod. The invention further provides a method for making the intermediates and a method for making 1H-imidazo(4,5-C)quinoline-4-amines via the intermediates.

11 Claims, No Drawings

PREPARATION OF 1H-IMIDAZO [4,5-C] QUINOLIN-4-AMINES VIA 1H-IMIDAZO [4,5-C] QUINOLIN-4-PHTHALIMIDE INTERMEDIATES

CROSS-REFERENCE TO RELATED APPLICATION

This application claims the benefit of provisional application Ser. No. 60/397,607, filed Jul. 23, 2002, the contents of which is incorporated herein.

FIELD OF THE INVENTION

The present invention relates to a process for the synthesis of 1H-imidazo[4,5-c]quinoline 4-phthalimide intermediates useful in preparing 1H-imidazo[4,5-C]quinoline 4-amines, a process for preparing 1H-imidazo[4,5-C]quinoline 4-amines using such intermediates; and, to the 1H-imidazo[4,5-c]quinoline 4-phthalimide intermediates. More particularly, the present invention relates to a novel process for the preparation of 1-isobutyl-1H-imidazo[4,5-C]quinoline 4-amine (Imiquimod) by introducing an amino group in the 4 position of 1-isobutyl-1H-imidazo[4,5-C]quinolin-4-amine via a 1-isobutyl-1H-imidazo[4,5-c]quinoline 4-phthalimide intermediate, and to the 1-isobutyl-1H-imidazo[4,5-c]quinoline 4-phthalimide intermediate.

BACKGROUND OF THE INVENTION

Imiquimod, 1-isobutyl-1H-imidazo[4,5-C]quinolin-4-amine, is an immune response modifier, useful for treating viral infections, such as genital warts. Imiquimod is disclosed in U.S. Pat. Nos. 4,689,338 and 5,238,944 and has the structure:

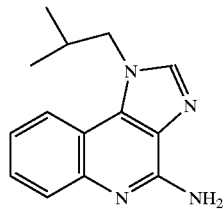

Several methods are known in the art for making 1H-imidazo[4,5-c]quinoline 4-amines, including Imiquimod. The amino group in the 4 position has been introduced in essentially three ways: The first is by nucleophilic substitution of a leaving group, e.g., Cl, triflate, etc., with ammonia, dibenzylamine or an azido group; the second is by reacting 1-isobutyl-1H-imidazo[4,5-c]quinoline-N-oxide with ammonium hydroxide or ammonium salts in the presence of tosyl chloride at 0–5° C.; and the third is by reacting 1-isobutyl-1H-imidazo[4,5-c]quinoline-N-oxide with benzoyl isocyanate.

Nucleophilic substitution reactions are disclosed in, for example, WO 97/48704, WO 92/06093, U.S. Pat. Nos. 5,395,937, 5,756,747, 4,988,815, 5,602,256, 5,578,727, 4,698,348, 4,689,388, European patents EP 145340, EP 0385630, EP 310950 and JP 04193866. Specifically, in WO 97/48704 the amino group is introduced by reaction of a 4-chloro derivative with sodium azide to obtain a tetrazole moiety. Reaction of the tetrazole moiety with triphenylphosphine gives the 4-amino derivative. In U.S. Pat. No. 5,395,937, a 4-triflate derivative is reacted with dibenzylamine. The catalytic reduction of the 4-dibenzylamino derivative places an amino group in the 4-position. U.S. Pat. No. 5,756,474, discloses a nucleophilic substitution with ammonia on a 4-chloro derivative, obtained by isomerization of 1-isobutyl-1H-imidazo[4,5-c]quinoline-N-oxide to the 4-hydroxy derivative, followed by reaction with $POCl_3$. The following patents all disclose a nucleophilic substitution of 1-isobutyl-1H-imidazo[4,5-c]quinoline-4-chloro with ammonia at high temperature and pressure: U.S. Pat. Nos. 4,988,815, 5,602,256, 5,578,727, 4,698,348, 4,689,388, EP 145340, JP 04193866, EP 0385630, and EP 310950.

WO 92/06093 discloses reacting 1-isobutyl-1H-imidazo[4,5-c]quinoline-N-oxide with ammonium hydroxide or ammonium salts in the presence of tosyl chloride at 0–5° C.

WO 92/15581 discloses reacting 1-isobutyl-1H-imidazo[4,5-c]quinoline-N-oxide with benzoyl isocyanate.

However, a need exists in the art for making 1H-imidazo[4,5-C]quinoline 4-amines, especially Imiquimod, in high purity and high yield and which does not require high temperature or pressure.

SUMMARY OF THE INVENTION

In one aspect, the present invention is directed to a compound of formula (II):

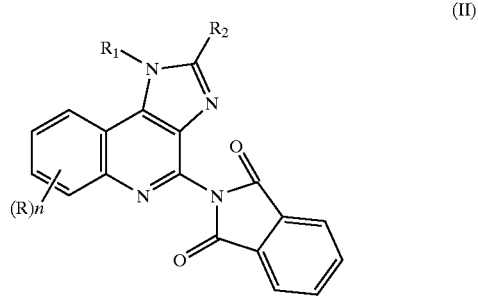

wherein $R_1$ is selected from the group consisting of: hydrogen; a straight or branched chain alkyl of one to about 10 carbon atoms, optionally substituted with a substituent selected from the group consisting of lower alkyl, cycloalkyl of 3 to about 6 carbon atoms, wherein said cycloalkyl is optionally substituted with a lower alkyl group; straight or branched chain alkenyl of 2 to about 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to about 6 carbon atoms, wherein said cycloalkyl is optionally substituted with a lower alkyl group; hydroxyalkyl of one to about six carbon atoms; acyloxyalkyl wherein the acyloxy moiety is alkanoyloxy of two to about four carbon atoms or benzoyloxy and the alkyl moiety contains one to about six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to about eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to about four carbon atoms; alkyl of one to about four carbon atoms; and halogen; and n is an integer from 0 to 2, with the proviso that if n is 2, then said groups together contain no more than 6 carbon atoms.

In a preferred embodiment, $R_1$ is isobutyl, $R_2$ is hydrogen, n is 0.

In another aspect, the present invention is directed to a process for preparing a 1H-imidazo[4,5-c]quinoline 4-phthalimide of formula (II) comprising reacting a compound of formula (III) with phthalimide in a suitable organic solvent, wherein R, $R_1$, $R_2$ and n are defined above.

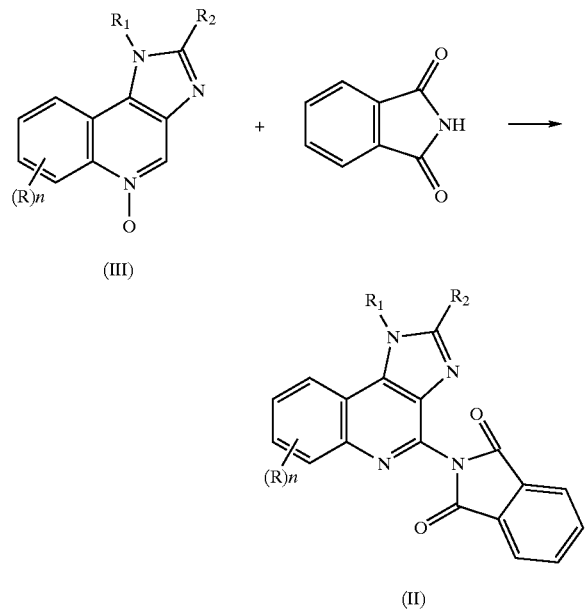

In another aspect, the present invention is directed to a process for preparing a compound of formula (I):

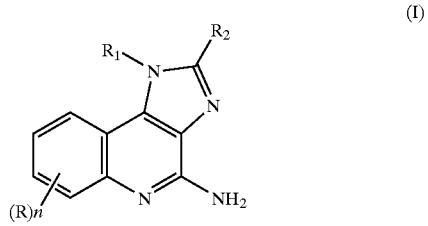

comprising reacting a compound of formula (II) with hydrazine hydrate in a suitable solvent, wherein R, $R_1$, $R_2$ and n are defined above.

These and other aspects of the present invention will now be described in more detail with reference to the following detailed description of the invention.

DETAILED DESCRIPTION OF THE INVENTION

In one aspect, the present invention is directed to a process for preparing 1H-imidazo[4,5-c]quinoline-4-amines of formula (I). The preferred 1H-imidazo[4,5-c]quinoline-4-amine is Imiquimod. However, the inventive process can be used to prepare any compound within the scope of formula (I), including those disclosed in U.S. Pat. Nos. 5,756,747, 5,395,937, 4,689,338, EP 385630, WO 97/48704, WO 92/06093 and WO 92/15581, all of which are incorporated by reference in their entirety herein.

The invention is also directed to novel 1H-imidazo[4,5-c]quinoline 4-phthalimide intermediates of formula (II), which are useful in preparing 1H-imidazo[4,5-c]quinoline-4-amines of formula (I), and to a process for preparing the intermediates of formula (II).

The 1H-imidazo[4,5-c]quinoline 4-phthalimide intermediates of formula (II) are prepared by reacting a 1H-imidazo[4,5-c]quinoline N-oxide of formula (II) with phthalimide. The reaction is carried out in a solvent and a base. Preferred solvents include methylene chloride and ethylacetate. Preferred bases include tri-n-butylamine, triethylamine and triisobutylamine. The most preferred mixture is ethylacetate and tri-n-butylamine. The reaction is preferably carried out in the presence of an organic acid halide, such as, benzoyl chloride. The reaction is preferably carried out at a temperature of between about 0–10° C., over a period of about one hour.

The 1H-imidazo[4,5-c]quinoline N-oxides of formula (III) can be obtained by any method known in the art, including those disclosed in: U.S. Pat. No. 5,756,747, WO 92/06093 and WO 92/15581; all of which are incorporated by reference in their entirety herein.

The 1H-imidazo[4,5-c]quinoline 4-phthalimide intermediates of formula (II) are then reacted with hydrazine hydrate in a suitable solvent to form 1H-imidazo[4,5-c]quinoline-4-amines of formula (I). Water is a preferred solvent. Preferably, isooctyl alcohol is added to avoid foam formation. The reaction is preferably carried out at a temperature of between about 94–95° C., over a period of about 4–5 hours.

One reaction scheme that may be used to make 1H-imidazo[4,5-c]quinoline-4-amines of formula (I) is shown below:

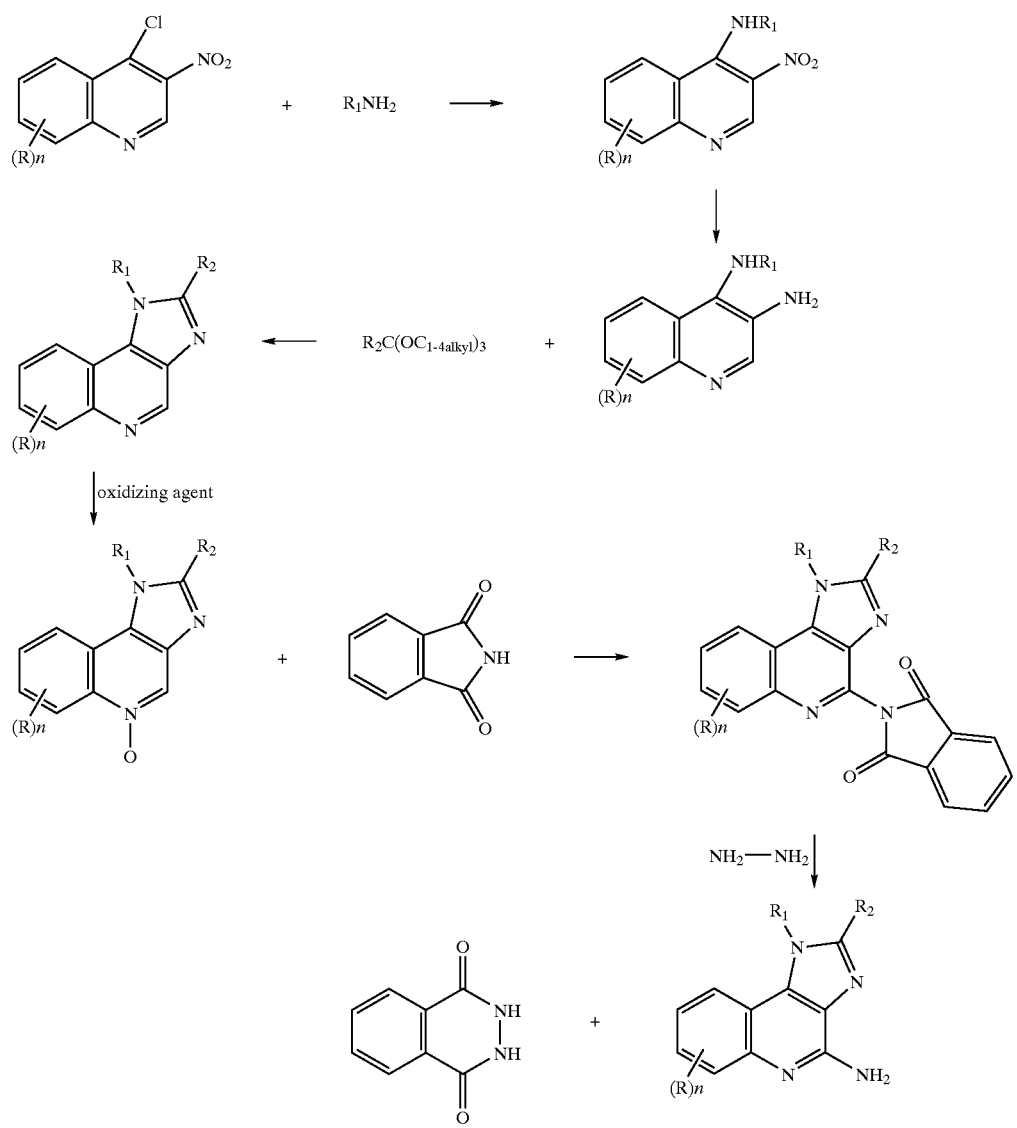

The present invention is illustrated in further detail with reference to the following non-limiting examples.

EXAMPLE 1

Preparation of 4-isobutyl-3-nitro quinoline 4-chloro-3-nitro-quinoline is reacted with isobutyl amine in the presence of triethylamine (TEA) at between −10 and +15° C. in toluene, while excluding moisture. After washing and phase separation, the organic solution is ready for the next step.

EXAMPLE 2

Preparation of 4-isobutyl-3-amino quinoline

The nitroxide group on the 4-isobutyl-3-nitro quinoline produced in Example 1 is reduced by catalytic reduction using toluene as solvent, Pd/C 5% (50% wet) as catalyst, at 40–45° C. and atmospheric pressure to produce 4-isobutyl 3-amino quinoline. The rate of reaction depends on efficiency of stirring. After catalyst filtration the solution is ready for the next step.

EXAMPLE 3

Preparation of 1-isobutyl-1H-imidazo[4,5-c] quinoline

The cyclization of 4-isobutyl 3-amino quinoline produced in Example 2 is carried out in toluene at 102–110° C. using TEOF (triethyl orthoformate) and 20% moles of formic acid to increase the rate of reaction, to produce 1-isobutyl-1H-imidazo[4,5-c]quinoline. Before addition of TEOF, in order to prevent its hydrolysis, it is necessary to remove water formed during the catalytic reduction by azeotropic distillation. A mixture of ethanol and toluene is distilled during the reaction to maintain the internal temperature at 102–110° C.

EXAMPLE 4

Preparation of 1-isobutyl-1H-imidazo[4,5-c] quinoline N-oxide

The oxidation of 1-isobutyl-1H-imidazo[4,5-c]quinoline produced in Example 3 is carried out in toluene at 40–45° C.

using peracetic acid as oxidant to produce 1-isobutyl-1H-imidazo[4,5-c]quinoline N-oxide. The product is isolated by filtration after addition of a sodium sulfate solution and ammonium hydroxide.

EXAMPLE 5

Preparation of 1-isobutyl-1H-imidazo[4,5-c]quinoline-4-phthalimide 93 ml of methylene chloride and 15 g of 1-isobutyl-1H-imidazo[4,5-c]quinoline N-oxide (HPLC=95%) are loaded into a 250 ml three necked round flask. Then 24.55 g of tri n-butylamine (98%) and 10.06 g of phthalimide (99%) are added to the flask under nitrogen and stirring. The suspension formed is cooled to 0° C. and the following solution is dropped into the suspension over 1 hour: 12.7 g of benzoyl chloride (98%) in 13 ml of methylene chloride, as the temperature is kept between 0–10° C. The mixture is stirred at room temperature for about 30 minutes and a sample is taken. HPLC analysis shows that there is 0.32% of the starting material, 87.72% of the target product, and 0.43% of the 4-hydroxy derivative. The solution is filtered and the filter cake is washed 3 times with 10 ml of methylene chloride. The wet filter cake is resuspended at 25° C. for at least 7 hours in 100 ml of methanol. After resuspension the solution is filtered and the filter cake is washed 2 times with 10 ml of methanol. Prior to the second filtration, HPLC shows that there is ≦0.4% of the starting material and ≦0.05% of the 4-hydroxy derivative. The solid is dried under vacuum at 50° C. for 15 hours. The dry solid weighs 18 g. HPLC analysis shows that the solid is 98.98% pure and the yield is 81.52% based on the starting material (1-isobutyl-1H-imidazo[4,5-c]quinoline N-oxide).

EXAMPLE 6

Preparation of 1-isobutyl-1H-imidazo[4,5-c]quinoline-4-amine 72 ml water and 18 g 1-isobutyl-1H-imidazo[4,5-c]quinoline-4-phthalimide (HPLC=98.98%) are heated to 70° C. in a 250 ml reactor. 4.8 g hydrazine hydrate is dropped into the reactor while stirring and then 2 ml iso-octyl alcohol is added to the reactor. The reaction mixture is heated at 94–95° C. for 4 hours and a sample is taken. HPLC analysis shows that there is 6.16% starting material and 94% target material. To obtain a complete conversion of starting material the reaction is allowed to proceed for another hour. The reaction mixture is cooled at 60° C. and 180 ml of methanol is added. The mixture is warmed at reflux for 15 minutes, then cooled at room temperature. The solution is filtered and the cake is washed 3 times with 15 ml of a 3.5:1 mixture of methanol and water. The wet solid obtained weighs 22.4 g. HPLC analysis shows that its purity is 98.23% (no phthalhydrazide integration). The wet solid is treated with 180 ml of water and 5.2 g of 37% HCl at 90–93° C. for 30 minutes. The hot suspension is filtered and the cake is washed 3 times with 15 ml of water. The solid is phthalhydrazide weighing 4.5 g. The hot solution is treated at 90–93° C. with 0.115 g $Na_2S_2O_4$ and 0.576 g charcoal. After 30 minutes the charcoal is filtered off and the cake is washed two times with 10 ml water. The solution is cooled at 70–75° C. and 10 g of 30% NaOH is added to pH 11.54, at which time a solid precipitates. The mixture is cooled to room temperature and after 1 hour the solid is filtered and the cake is washed 3 times with 10 ml water. 15.1 g of crude wet Imiquimod (pale pink color) is obtained. The Imiquimod is dried to a weight of 10.57 g. HPLC shows the purity to be 98.12%. There is 1.55% phthalhydrazide present.

EXAMPLE 7

Purification of 1-isobutyl-1H-imidazo[4,5-c]quinoline-4-amine 53.55 ml water, 23.62 ml butyl alcohol, 10.57 crude Imiquimod and 4.77 g of 37% HCl are loaded into a 100 ml reactor. The mixture is heated to 55–60° C. to obtain a solution. The solution is cooled to room temperature and a white crystal precipitates. The solid is filtered and washed 2 times with 5 ml butyl alcohol. 13.63 g of wet Imiquimod chloridrate is obtained. HPLC analysis shows that there is 99.89% Imiquimod and 0.01% phthalhydrazide. 120 ml water and 13.63 g of wet Imiquimod chloridate are loaded into a 250 ml reactor and heated to 85–90° C. The hot solution is filtered and the cake is washed with 5 ml of hot water. Then 0.024 g of $Na_2S_2O_4$ is added. The colorless solution is cooled to 70–75° C. and 5.3 g of 30% NaOH is added to provide a pH of 9.7, at which point a solid precipitates. The suspension is cooled to 20° C. and filtered. The cake is washed 3 times with 5 ml water and twice with 5 ml methanol. During the washes no chloride was detected by silver nitrate. The solid is dried under vacuum at 50° C. for 8 hours. 8.98 g of Imiquimod (off-white color) is obtained. HPLC shows the purity to be 99.94% and the yield to be 63.3% based on the starting material (1-isobutyl-1H-imidazo[4,5-c]quinoline N-oxide).

Having thus described the invention with reference to particular preferred embodiments and illustrated it with examples, those of skill in the art may appreciate modifications to the invention as described and illustrated that do not depart from the spirit and scope of the invention as disclosed in the specification.

What is claimed is:

1. A compound of formula (II):

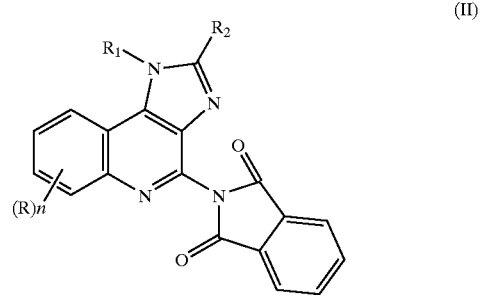

(II)

wherein
  $R_1$ is selected from the group consisting of: hydrogen; a straight or branched chain alkyl of one to about 10 carbon atoms, optionally substituted with a substituent selected from the group consisting of lower alkyl, cycloalkyl of 3 to about 6 carbon atoms, wherein said cycloalkyl is optionally substituted with a lower alkyl group; straight or branched chain alkenyl of 2 to about 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to about 6 carbon atoms, wherein said cycloalkyl is optionally substituted with a lower alkyl group; hydroxyalkyl of one to about six carbon atoms; acyloxyalkyl wherein the acyloxy moiety is alkanoyloxy of two to about four carbon atoms or benzoyloxy and the alkyl moiety contains one to about six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to about eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to about four carbon atoms; alkyl of one to about four carbon atoms; and halogen; and n is an integer from 0 to 2, with the proviso that if n is 2, then said groups together contain no more than 6 carbon atoms.

2. A compound of claim 1, wherein $R_1$ is isobutyl, $R_2$ is hydrogen, and n is 0.

3. A process for preparing a 1H-imidazo[4,5-c]quinoline 4-phthalimide of formula (II):

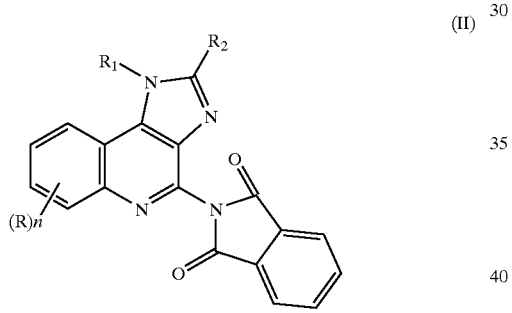

(II)

comprising reacting a compound of formula (III);

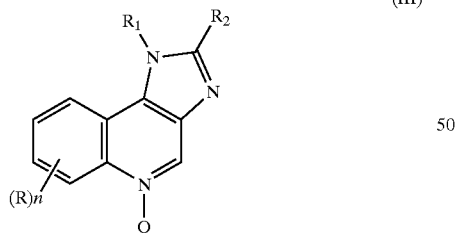

(III)

with phthalimide, wherein $R_1$ is selected from the group consisting of: hydrogen; a straight or branched chain alkyl of one to about 10 carbon atoms, optionally substituted with a substituent selected from the group consisting of lower alkyl, cycloalkyl of 3 to about 6 carbon atoms, wherein said cycloalkyl is optionally substituted with a lower alkyl group; straight or branched chain alkenyl of 2 to about 10 carbon atoms, wherein the olefinic unsaturation in the alkenyl group is at least one carbon atom removed from the 1-nitrogen, and wherein the straight or branched chain alkyl is optionally substituted with a substituent selected from the group consisting of lower alkyl, cycloalkyl of 3 to about 6 carbon atoms, wherein said cycloalkyl is optionally substituted with a lower alkyl group; hydroxyalkyl of one to about six carbon atoms; acyloxyalkyl wherein the acyloxy moiety is alkanoyloxy of two to about four carbon atoms or benzoyloxy and the alkyl moiety contains one to about six carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

$R_2$ is selected from the group consisting of: hydrogen; straight or branched chain alkyl containing one to about eight carbon atoms; benzyl; (phenyl)ethyl; and phenyl, wherein said benzyl, (phenyl)ethyl and phenyl substituents are optionally substituted on the benzene ring by one or two moieties independently selected from the group consisting of lower alkyl, lower alkoxy, and halogen, with the proviso that when the benzene ring is substituted by two such moieties, then the moieties together contain more than 6 carbon atoms;

R is independently selected from the group consisting of: alkoxy of one to about four carbon atoms; alkyl of one to about four carbon atoms; and halogen; and n is an integer from 0 to 2, with the proviso that if n is 2, then said groups together contain no more than 6 carbon atoms.

4. The process of claim 3, wherein $R_1$ is isobutyl, $R_2$ is hydrogen, and n is 0.

5. The process of claim 3 or claim 4, wherein the reaction takes place in the presence of a base and a solvent.

6. The process of claim 5, wherein the solvent is selected from the group consisting of methylene chloride and ethylacetate and the base is selected from the group consisting of tri-n-butylamine, triethylamine, and triisobutylamine.

7. The process of claim 6, wherein the solvent is ethylacetate and the base is tri-n-butylamine.

8. The process of claim 5, wherein the reaction further takes place in the presence of an organic acid halide.

9. The process of claim 8, wherein the organic acid halide is benzoyl chloride.

10. The process of claim 3 or claim 4, wherein the reaction takes place at a temperature of between about 0 to about 10° C.

11. The process of claim 3 or claim 4, wherein the compound of formula (III) and phthalimide are reacted over a period of about 1 hour.

* * * * *